United States Patent [19]

Ishihara et al.

[11] Patent Number: 4,668,665
[45] Date of Patent: May 26, 1987

[54] FORMULATION OF SUCRALFATE

[75] Inventors: Kouji Ishihara, Saitama; Kazuo Igusa; Toshichika Ogasawara, both of Tokyo, all of Japan

[73] Assignee: Chugai Seiyaku Kabushiki Kaisha, Tokyo, Japan

[21] Appl. No.: 775,935

[22] Filed: Sep. 10, 1985

Related U.S. Application Data

[63] Continuation of Ser. No. 543,450, Oct. 19, 1983, abandoned.

[30] Foreign Application Priority Data

Oct. 27, 1982 [JP] Japan ................. 57-187614

[51] Int. Cl.$^4$ ................. A61K 31/70; A61K 31/195
[52] U.S. Cl. ................. 514/53; 514/561; 514/566; 514/970
[58] Field of Search ................. 514/53, 561, 566, 970

[56] References Cited

U.S. PATENT DOCUMENTS 3,432,489  3/1969  Nitta et al. .................. 424/180

FOREIGN PATENT DOCUMENTS 2425264  5/1973  Fed. Rep. of Germany ...... 424/180
2356418  1/1976  France .................. 424/180

OTHER PUBLICATIONS

Chem. Abstracts, vol. 92 170377c, Citation of Nagashima et al, Arzneim–Forsch, 1980, 30(1) 80–3.
Chem Abstracts, vol. 87:181372n, Citation of Yamskova et al, Mol. Biol. (Moscow) 1977, 11(5) 1147–54.
Chem. Abstracts, vol. 95:2203d, Citation of Waite et al., Science 1981, 212 (4498) 1038–40.
Nagashima et al, Arzneim.-Forsch./Drug Res. 30(1), 1, 88–91 (1980).
Sasaki et al, paper entitled "Binding of Sucralfate to Duodenal Ulcer in Man".
Nagashima et al, Arzneim.-Forsch./Drug Res. 30(1), 1, 84–88 (1980).
Nagashima et al, Arzneim.-Forsch./Drug Res. 30(1), 1, 80–83 (1980).
Nagashima et al, Arzneim.-Forsch./Drug Res. 29(11), 11, 1668–1676 (1979).
Nakazawa et al, Digestive Diseases and Sciences, vol. 26, No. 4 (Apr. 1981).
Nagashima, J. Clin. Gastroenterol 3 (Suppl 2):103–110, 1981.
Nagashima, J. Clin. Gastroenterol 3 (Suppl 2):117–127, 1981.

*Primary Examiner*—Donald B. Moyer
*Assistant Examiner*—Jacqueline M. Stone
*Attorney, Agent, or Firm*—Morgan & Finnegan

[57] ABSTRACT

A storage-stable sucralfate-containing preparation which maintains its ability, even after extended periods of time, to form a viscous, sticky, paste-like material in the presence of gastric secretions is disclosed as well as the method of making same.

3 Claims, No Drawings

FORMULATION OF SUCRALFATE

This is a continuation, of application Ser. No. 543,450 filed Oct. 19, 1983, now abandoned.

BACKGROUND OF THE INVENTION

The present invention relates generally to storage-stable sucralfate preparations and, more particularly, to sucralfate-containing compositions which retain their ability to form viscous, sticky, paste-like compositions in the presence of gastric secretions. These compositions are characterized by the inclusion of a material which helps to preserve the adhesive nature of sucralfate and the protective effects of sucralfate against acids, pepsin and bile salts. These preparations, because of this property, exhibit a sustained effect in protecting the disrupted mucosa which are characteristic of peptic ulcers, and, to a lesser degree, chronic gastritis.

An aluminum salt of sucrose sulfate ester (conventionally known as sucralfate) is an excellent ulcer curative agent with minimal side effects, and is extensively used in anti-ulcer therapy. See, for example, U.S. Pat. No. 3,432,489 which is incorporated by reference herein.

Peptic ulcers and chronic gastritis are exacerbated by the pepsin and hydrochloric acid which occur naturally in gastric juice. By virtue of its pepsin-binding and antacidic properties, sucralfate inhibits the pathogenetic activities of pepsin and hydrochloric acid in peptic ulcer and chronic gastritis, and thereby assists the natural healing process. Sucralfate also promotes revascularization and regeneration of ulcerated mucosal tissue.

Beyond these effects, the most characteristic feature of sucralfate which sets it apart from other anti-ulcer agents is its ability to selectively bind to the ulcer-affected mucosa of the stomach and duodenum rather than to normal gastrointestinal tissues, thus forming a protective coating which is impervious to pepsin and stomach acid and allowing normal healing to ensue.

Sucralfate forms a sticky paste in an acidic solution at a pH below 4.0. When administered orally, sucralfate reacts with gastric juice in the stomach to form a sticky paste which binds to the ulcer-affected part of the stomach or duodenum to exhibit a sustained effect to protect the mucosa in that part. This effect of sucralfate can be confirmed in vitro by the following procedure:

According to the Japanese Pharmacopoeia (10th ed.), 1,000 ml of artificial gastric juice (pH: ca. 1.2) is prepared from a mixture of sodium chloride (2.0 g), dilute hydrochloric acid (24 ml) and water. Sucralfate (1 g) is suspended in 10 ml of the gastric juice in a test tube, and immediately thereafter, sucralfate forms a sticky paste which adheres to the inner surface of the test tube as if sucralfate administered orally contacted acid in the stomach and formed a viscous paste.

In the course of these in vitro studies on sucralfate, it has unexpectedly been found that an aqueous suspension of sucralfate or a solid preparation thereof placed under hot and humid conditions loses partly, or entirely, the most characteristic feature of sucralfate (ability to form a sticky paste in the artificial gastric juice) although its other properties remain substantially unchanged. In particular, this phenomemon occurs in the aqueous suspension in about 15 to 20 days after its preparation, and sucralfate particles remain suspended even if the suspension is mixed with the artificial gastric juice. Animal experiments were conducted with rats in which ulcers were artificially induced, and confirmed that sucralfate preparations with reduced ability to form a viscous paste were not highly effective in protecting the ulcer-affected mucosa from attacking factors.

SUMMARY OF THE INVENTION

Various efforts were made to produce a sucralfate preparation that retains its ability, even after extended periods of time, to form a viscous paste in gastric juice. As a result, it was found that this object can be achieved by adding to sucralfate a material which helps to preserve the adhesive nature of sucralfate and protects the effect of sucralfate against acids, pepsin and bile salts, the latter ingredients commonly found in the digestive tract.

DETAILED DESCRIPTION OF THE INVENTION

In accordance with this invention, such material can be selected and evaluated by a facile, in-vitro test. Specifically, to an aqueous suspension of sucralfate is added the selected adhesive-preservation material and the resulting suspension is permitted to stand at room temperature for about 15–30 days. After stirring, a small portion, i.e. about 2 ml is placed in a test tube and artificial gastric juice (about 20 ml) is added and the mixture stirred. A positive test results in the formation of a sticky paste which adheres to the inner surface of the test tube in contrast to the control (no adhesive preservation) which forms no deposit on the test tube surface.

In one embodiment, it is found that certain amino acids are highly effective for this purpose. They include neutral amino acids free from benzene ring in the chemical structure, as well as acidic and basic amino acids free from benzene ring, and salts thereof. However, amino acids containing sulfur atoms in their chemical structure are not desirable since their mixture with sucralfate develops a color in the course of time.

Suitable amino acids that may be used in the present invention include neutral amino acids such as glycine, alanine, valine, serine, proline, glutamine, asparagine, aminobutyric acid and $\epsilon$-aminocaproic acid; acidic amino acids such as glutamic acid and aspartic acid and salts thereof; basic amino acids such as lysine, arginine and histidine and salts thereof. Also effective are compounds which contain these amino acid structures in their structure, such as pantothenic acid having the $\beta$-alanine moiety and salts thereof, and N-glycylglycine having the glycine moiety.

According to the present invention, sucralfate may be mixed with the adhesive-preservation material in any proportions so long as the desired effect of the material is attained by mixing. Generally, the amount of adhesive-preservation material is about 0.5 to 50 weight percent of sucralfate, and about 1 to 10 weight percent is preferred. In order to form an aqueous suspension of sucralfate, a suitable adhesive-preservation material may be dissolved in a dispersion medium together with sucralfate. If a solid preparation is desired, a uniform mixture of sucralfate and the adhesive preservation material is first prepared by dissolving the material in water or a common binder, then sucralfate is mixed with the solution, and the mixture is finally formulated by a conventional technique to make a desired preparation in the form of tablets, capsules, granules or subtilized granules. The sucralfate preparations in either form proved to be highly stable for an extended period without losing the ability to form a sticky paste in artificial gastric juice. In addition, there was no decrease in the ability of sucralfate to protect the mucosa of the digestive tract in animals or humans.

The advantages of the present invention are hereunder described in greater detail by reference to working examples, to which the scope of the invention is by no means limited.

EXAMPLE 1

To a mixture of sucralfate (100 g), glycerin (200 g), 70% D-sorbitol (200 g) and an antiseptic (1.2 g), distilled water was added to make 1,000 ml. The mixture was well stirred with an agitating/homogenizing mixer to form a suspension. The suspension was divided into two equal portions (500 ml each). To one portion, β-alanine (2.5 g) was added and the mixture was well stirred. The two portions of the suspension were left to stand at room temperature for 30 days until they separated into liquid and solid phases. Each portion was stirred to restore a uniform suspension. Two milliliters of each suspension were placed in a test tube, and artificial gastric juice (20 ml) was added to each suspension, and the mixture was stirred. In the suspension containing β-alanine, sucralfate formed a sticky paste that adhered to the inner surface of the test tube and the supernatant remained also clear. However, there was no change in the β-alanine free suspension and no deposit was formed on the inner surface of the test tube.

EXAMPLE 2

To the solution of L-proline (300 g) in pure water (11,000 ml), sucralfate (5,000 g) was added, and the resulting dispersion was dried with a spray dryer to form a granular powder. As a control, a granular powder free from L-proline was prepared in the same manner. The two samples of granular powder were left to stand for 30 days at 40° C. and 85% relative humidity. Thereafter, a 1 g portion of each sample was placed in a test tube, mixed with 10 ml of artificial gastric juice, and the mixture was stirred. In the sample containing L-proline, a sticky paste formed and adhered to the inner surface of the test tube. However, the granules of the control sample remained suspended in the gastric juice.

EXAMPLE 3

Sucralfate preparations containing amino acids indicated in the following table (for their amounts, also see the table) were formulated as in Example 1 and subjected to an accelerated test, In each sample, sucralfate exhibited sustained ability to form a sticky paste under acidic conditions.

TABLE

| Amino acids | Effective amount (wt % relative to sucralfate) |
|---|---|
| L-alanine | >0.5 |
| γ-aminobutyric acid (n) | |
| glycine | >1 |
| ε-aminocaproic acid | |
| DL-alanine | |
| L-argine | >3 |
| L-arginine hydrochloride | |
| L-lysine hydrochloride | |
| L-aspartic acid | |
| sodium L-aspartate | |
| L-glutamic acid | |
| L-histidine hydrochloride | |
| L-glutamine, L-asparagine, | >5 |
| L-serine, DL-valine, | |
| L-proline | |

It should be understood by those skilled in the art that various modifications may be made in the present invention without departing from the spirit and scope thereof as described in the specification and defined in the appended claims.

What is claimed is:

1. A storage-stable, sucralfate-containing composition which maintains its ability, even after extended periods of time of at least 15 days, to form a viscous, sticky, paste-like composition in the presence of artificial gastric secretion, which contains, in addition to sucralfate, a material which helps to preserve the adhesive nature of sucralfate and the protective effects of sucralfate against acids, pepsin and bile salts wherein said material is an amino acid selected from glycine, alanine, valine, serine, proline, glutamine, asparagine, arginine, aminobutyric acid, ε-aminocaproic acid, glutamic acid, aspartic acid, lysine or histidine, or their acid and base addition salts, or a compound which contains in its structure an amino acid selected from pantothenic acid or N-glycylglycine or their acid and base addition salts, said composition containing said amino acid or compound in 0.5 to 50 weight percent based on the amount of sucralfate.

2. The composition of claim 1 which contains said amino acid or compound in 1 to 10 weight percent based on the amount of sucralfate.

3. A pharmaceutically acceptable composition comprising an inert carrier and a mucosal protecting amount of a sucralfate composition as claimed in claim 1.

* * * * *